United States Patent [19]
Gordon et al.

[11] Patent Number: 6,080,915
[45] Date of Patent: Jun. 27, 2000

[54] CONSTRUCTS ENCODING DEGRADATION ENZYMES FOR AROMATIC COMPOUNDS AND TRANSGENIC PLANTS CONTAINING SAME

[75] Inventors: Irving Gordon, Niagara Falls; Stanley A. Sojka, Buffalo, both of N.Y.; Milton P. Gordon, Seattle, Wash.

[73] Assignee: Occidental Chemical Corporation, Dallas, Tex.

[21] Appl. No.: 07/670,644

[22] Filed: Mar. 18, 1991

Related U.S. Application Data

[63] Continuation-in-part of application No. 07/369,886, Jun. 22, 1989, abandoned.

[51] Int. Cl.$^7$ .......................... C12N 15/31; C12N 15/53; C12N 15/82; C12N 15/84; A01H 5/00
[52] U.S. Cl. .................. 800/300; 800/278; 800/288; 800/294; 800/317.3; 800/323; 435/69.1; 435/190; 435/252.2; 435/252.3; 435/320.1; 435/418; 435/419; 435/468; 435/469; 210/602
[58] Field of Search .................. 435/240.4, 317.1, 435/172.1, 252.3, 69.1, 190, 252.2, 320.1, 418, 419, 468, 469; 536/27; 800/200, 278, 288, 294, 300, 317.3, 323; 935/59; 210/602

[56] References Cited

U.S. PATENT DOCUMENTS

| | | | |
|---|---|---|---|
| 4,407,956 | 10/1983 | Howell | 435/172 |
| 4,459,355 | 7/1984 | Cello et al. | 435/172.3 |
| 4,508,824 | 4/1985 | Olsen | 435/172.3 |
| 4,535,060 | 8/1985 | Comai | 435/172.3 |
| 4,536,475 | 8/1985 | Anderson | 435/172.3 |
| 4,581,847 | 4/1986 | Hibberd et al. | 47/58 |
| 4,658,082 | 4/1987 | Simpson et al. | 800/1 |
| 4,678,582 | 7/1987 | Lavigne | 435/262 |
| 4,693,976 | 9/1987 | Schilperoort et al. | 435/172.3 |
| 4,757,011 | 7/1988 | Chaleff et al. | 435/172.1 |
| 4,762,785 | 8/1988 | Comai | 435/172.3 |
| 4,795,855 | 1/1989 | Fillatti et al. | 800/1 |
| 4,801,540 | 1/1989 | Hiatt et al. | 435/172.3 |
| 4,810,648 | 3/1989 | Stalker | 435/191 |

FOREIGN PATENT DOCUMENTS

| | | |
|---|---|---|
| 87-74947 | 6/1986 | Australia . |
| 172506 | 8/1985 | European Pat. Off. . |
| 159884 | 10/1985 | European Pat. Off. . |
| 229042 | 1/1987 | European Pat. Off. . |
| 251654 | 6/1987 | European Pat. Off. . |
| 270355 | 12/1987 | European Pat. Off. . |
| 289478 | 11/1988 | European Pat. Off. . |
| 61-257186 | 11/1986 | Japan . |
| WO/8402919 | 8/1984 | WIPO . |

OTHER PUBLICATIONS

Ghosal et al 1985 Science 228: 135–142.
Ghosal et al 1988 MolGen Genet 211:113–120. (Jan.).
Frantz et al 1987 Proc Natl Acad Sci USA 84: 4460–4464.
Botterman et al 1988 Trends in Genetics 4: 219–222. (Aug.).
Zukowski et al 1983 Proc Natl Acad Sci USA 80:1101–1105.
Perkins 1987, The Molecular Biol. of Halogenated Aromatic Catabolic Plasmid pJP4; UMI Dissertation Information Services #8813086.
Don et al 1985 J. Bacti 161:85–90.
Harayama et al 1987 Molec Gen Genetics 210:241–247.
Qun Zhu, et al., Expression of the Xyle Gene in *Agrobacterium Tumefaciens*: Construction of Multipurpose Cloning Vectors, 3–4 *Biochemical Genetics* (1988).
John Fletcher, et al., "Polychlorobiphenyl (PCB) Metabolism by Plant Cells," *Biotechnology Letters*, vol. 9, No. 11, pp. 817–820 (1987).
David M. Stalker, "Herbicide Resistance in Transgenic Plants Expressing a Bacterial Detoxification Gene," *Science*, pp 419–423 (1988).
Dilip M. Shah, et al., "Engineering Herbicide Tolerance in Transgenic Plants," *Science* vol. 233, pp. 478–481 (1986).
Andrea Barta, et al., "The Expression of a Nopaline Synthase–Human Growth Hormone Chimaeric Gene in Transformed Tobacco and Sunflower Callus Tissue," *Plant Molecular Biology* 6:347–357 (1986).
Jerzy Paszkowski, et al., "Direct Gene Transfer to Plants," *The MBO Journal*, vol. 3, No. 12, pp 2717–2722 (1984).
R. Hain, et al., "Uptake, Integration, Expression and Genetic Transmission of a Selectable Chimaeric Gene by Plant Protoplasts," *Mol Gen Genet*, 199: 161–168 (1985).
Jozef St. Schell, "Transgenic Plants as Tools to Study the Molecular Organization of Plant Genes," *Science*, vol. 237, pp 1176–1183 (1987).
N.E. Olszewski, et al., "Specialized Binary Vector for Plant Transformation Expression of the Arabidopsis–Thialana AHAS Gene in Nicotiana–Tobacum," *Biosis* 89: 73275 (1988).
M. DeBlock, et al., "Engineering Herbicide Resistance in Plants by Expression of a Detoxifying Enzyme," Plant Genetic Systems N.V., J. Tlateaastraat 22, B–9000, GENT, Belgium, p. 2513–2518 (1987).
E. J. Perkins, et al., "Use of *Alcaligenes eutrophus* as a Source of Genes for 2,4–D Resistance in Plants," *Weed Science*, vol. 35 (Suppl. 1): 12–18 (1987).
A.J.M. Matzke et al, "A Set of Novel Ti Plasmid–Derived Vectors for the Production of Transgenic Plants," *Plant Molecular Biology* 7:357–365 (1986).

*Primary Examiner*—David T. Fox
*Attorney, Agent, or Firm*—Anne E. Brookes; Richard D. Fuerle

[57] ABSTRACT

Disclosed is a plant transformation construct comprising DNA having (1) a ring-opening gene that encodes an enzyme that can open an aromatic ring, (2) upstream of the ring-opening gene, a eukaryotic promoter, and (3) downstream of said ring-opening gene, a polyadenylic acid addition site.

Also disclosed is a plasmid that contains the plant transformation construct and bacteria that contain the plasmid. A transgenic plant cell that contains, as part of its genome, the plant transformation construct is also disclosed, and a transgenic plant is grown from the transgenic plant cell. Also disclosed is a method of degrading aromatic compounds in soil by planting the transgenic plant in the soil.

23 Claims, No Drawings ns(1) 6,080,915

CONSTRUCTS ENCODING DEGRADATION ENZYMES FOR AROMATIC COMPOUNDS AND TRANSGENIC PLANTS CONTAINING SAME

This application is a file wrapper continuation-in-part of application Ser. No. 07/369,886, filed Jun. 22, 1989, now abandoned.

BACKGROUND OF THE INVENTION

This invention relates to plant transformation constructs containing genes that encode enzymes that can open aromatic rings. It also relates to the insertion of these genes into plant cells, and to the regeneration of those cells into transgenic plants that can degrade aromatic compounds in soil by opening an aromatic ring.

As a result of spills, accidents, construction, the use of outdoor storage ponds, poorly controlled manufacturing processes, and the deliberate use of herbicides and pesticides, aromatic compounds have found their way into soil in concentrations considered to be environmentally hazardous. Not only are these compounds often malodorous and the source of health problems, but, in high concentrations, they can represent a fire hazard. Moreover, the compounds are not readily biodegraded and persist for many years.

Over time, these aromatic compounds can seep into the ground water from which many municipalities in the United States draw their drinking water. Because the compounds tend to accumulate in fatty tissue and may be hazardous, it is necessary to remove them from the water and prevent them from entering the food chain. As a consequence, there is considerable pressure from government agencies to remove these aromatic compounds from the soil, where they are more concentrated, before they can enter the ground water. This can be an expensive process because the compounds are usually present in very low concentrations.

The removal and destruction of these compounds in soil is a formidable task. If the compounds are volatile they can sometimes be stripped from the soil with air or, if they are soluble, they can sometimes be removed by solvent extraction; but, after removal, it is still necessary to degrade or destroy them. Degradation in the soil is difficult as it requires a chemical reaction. Since the aromatic compounds are usually present in small concentrations, and various other reactive organic compounds are also present in the soil, a large quantity of chemicals is required for effective treatment. Incineration of the soil is effective in destroying the aromatic compounds but is very expensive and is impractical when the aromatic compounds are present in low levels.

Certain bacteria and fungi are known to produce enzymes that are capable of degrading aromatic compounds, including chlorinated aromatic compounds. While the use of bacteria has some advantages over other methods of degrading aromatic compounds in soil, bacterial remediation is not without its problems. (See, for example, "Bioengineering Issues Related to in situ Remediation of Contaminated Soils and Groundwater," by Perry L. McCarty, *Environmental Biotechnology*, ed. by Gilbert S. Omenn, Plenum Press (1988)). First, it is usually necessary to use aerobic bacteria because anaerobic bacteria work too slowly and are not effective near the surface of the soil where oxygen penetrates. On the other hand, aerobic bacteria are effective only near the surface of the soil, and, in order to increase their penetration into the soil, it is necessary to aerate the soil, which adds to the expense of the process. These bacteria are specially selected and propagated and are usually not only quite expensive, but are also required to be used in large amounts in order to effectively treat a contaminated area. Moreover, once released into the environment, it is difficult to contain them and prevent them from spreading out to other areas. As a result, the use of bacteria creates regulatory problems and can arouse public opposition which further adds to the cost of treating contaminated soil.

What is needed is an inexpensive, safe, and effective method of degrading aromatic compounds in soil without the addition of chemicals or microorganisms to the soil. Until now, no such method has been found.

SUMMARY OF THE INVENTION

We have developed a novel plant transformation construct which can be used to transform plant cells. Plants regenerated from those cells are capable of degrading aromatic compounds by opening the aromatic ring. When these transgenic plants are planted in soil contaminated with aromatic compounds, they remove the aromatic compounds from the soil and degrade them by opening the aromatic ring.

In a further very surprising discovery, we have found that not only is the aromatic ring opened by the transgenic plants of this invention, but the aromatic compound is "mineralized," by which it is meant that the aromatic compound is degraded all the way to inorganic compounds such as halide salts, carbon dioxide, and water. As a result, the aromatic compounds are not only removed from the soil but are also converted to safe and harmless materials.

Unlike many other processes for treating soil contaminated with aromatic compounds, the use of the transgenic plants of this invention does not involve the addition of chemicals or microorganisms to the soil. And, because plants such as trees can be used, which have a very deep aerobic root system, the soil can be treated from its surface down to as much as about 20 feet or more.

DETAILED DESCRIPTION OF THE INVENTION

The plant transformation construct of this invention comprises one strand or two complementary strands of deoxyribonucleic acid (DNA). The construct has at least three components: (1) a gene that encodes an enzyme that can open an aromatic ring, (2) a eukaryotic promoter, and (3) a polyadenylic acid addition site. The construct may also can contain various other optional components.

ESSENTIAL COMPONENTS

The ring-opening gene encodes an enzyme that can open an aromatic ring. The starting sequence of the ring-opening gene should be compatible with plant translation machinery. Typically, this means that it should preferably have an ATG (adenine-thymine-guanine) sequence to initiate translation with no other ATG sequence between the start of transcription and the first ATG of the coding sequence. Preferably, this gene encodes an enzyme that can open a halogenated aromatic ring, and most preferably a chlorinated aromatic ring. While the ring-opening gene may encode an enzyme that can open heterocyclic rings, it is preferably active against carbocyclic aromatic rings because carbocyclic aromatic compounds are more commonly found in contaminated sites. Also, for the same reason, the gene is preferably active against single aromatic rings, but some ring-opening enzymes also degrade multiple aromatic rings, opening one ring at a time. Examples of aromatic compounds that can be degraded by enzymes include benzene, toluene, xylene, benzpyrenes, catechols, halogenated catechols, benzoic acids such as 3-chlorobenzoic acid and 4-chlorobenzoic acid, phenols such as pentachlorophenol, polynuclear aromatics such as anthracene and naphthalene, and heterocyclics such as pyrimidines. More than one aromatic ring-opening gene can be included in the construct in order to enable the resulting transgenic plant to degrade a variety of aromatic compounds.

Genes that encode enzymes that degrade aromatic compounds are obtainable from various organisms such as, for example, Alcaligenes, Flavobacterium, Corynebacterium, Arthrobacter, Aspergillus, *Klebsiella oxytoca*, and Pseudomonas bacteria, particularly *Pseudomonas putida, cepacia*, and *fluorescens*. See, for example, U.S. Pat. Nos. 4,493,895; 4,803,166; 4,761,376; 4,477,570; 4,511,657; and 4,508,824, an article by D. Ghosal et al. titled "Microbial Degradation of Halogenated Compounds," *Science*, 228, No. 4696 (1985) pages 135 to 142, and "Constructing Microbial Strains for Degradation of Halogenated Aromatic Hydrocarbons," by Peter J. Chapman, *Basic Life Sciences, Environmental Biotechnology, Reducing Risks From Environmental Chemicals Through Biotechnology*, Volume 45, pages 81–95, given by Frantz ibid." and substitute ed. Gilbert S. Omenn, Plenum Press (1988), herein incorporated by reference. They can also be obtained from fungi (see U.S. Pat. No. 4,554,075), from some plants, and from some animals. The genes described in this patent can also be acquired by requesting the genes, or plasmids bearing the genes, from the inventors, who have published research articles describing the isolation and characterization of the genes (e.g., Perkins, E. J., Gordon, M. P., Caceras, O., Lurquin, P. F. (1990) "Organization and Sequence Analysis of the 2,4-Dichlorophenol Hydroxylase and Dichlorocatechol Oxidative Operons of Plasmid pJP4," *J. Bacteriol.* 172:2351–2359). Using published sequences, a person skilled in the art could isolate the genes by polymerase chain reaction amplification of the desired sequence, allowing rapid cloning of the gene into a plant expression vector readily available from commercial companies (i.e., Pharmacia). Alternatively, the published sequence can be used to cut the plasmid with commercially available restriction enzymes to give a DNA fragment containing the desired gene. The undesired nucleotides can be trimmed off using exonuclease III to give the genomic DNA sequence which can be inserted into the plant expression vector.

This invention is particularly concerned with genes that encode catechol dioxygenase enzymes that can open the aromatic ring of catechols or halogenated catechols, particularly chlorinated catechols, because catechols almost always lie on the degradative pathway of aromatic compounds. Any gene that encodes a catechol dioxygenase can be used in this invention. Examples of such enzymes include chlorocatechol 1, 2-dioxygenase, also known as catechol 1,2-dioxygenase II or pyrocatechase II. The nucleotide sequence for this enzyme (from the plasmid pJP4 of *Alcaligenes eutrophus*) is given by D. Ghosal and You, "Nucleotide Homology and Organization of Chlorocatechol Oxidation Genes of Plasmids pJP4 and pAC27," *Mol. Gen. Genet*. 211: 113–120 (1988). The entire sequence of the operon is given by B. Frantz et al. in "Organization and Nucleotide Sequence Determination of a Gene Cluster Involved in 3-Chlorocatechol Degradation," Proc. Natl. Acad. Sci. U.S.A. 84(13) 4460-4 (1987).

For example, this enzyme catalyzes the following reactions:

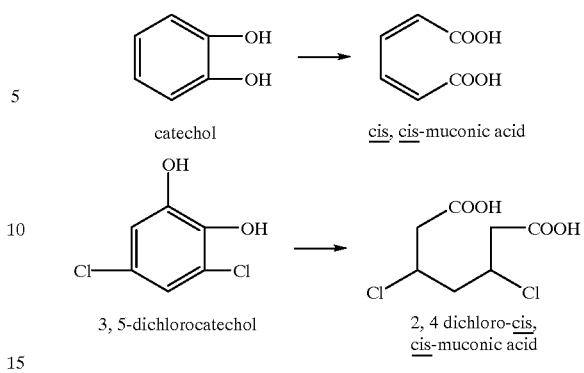

This enzyme will also open the aromatic ring of brominated catechols. For a source of the gene encoding dichlorocatechol 1,2-dioxygenase see, "Transposon Mutagenesis and Cloning Analysis of the Pathways for Degradation of 2,4-Dichlorophenoxyacetic Acid and 3-Chlorobenzoate in *Alcaligenes eutrophus* JMP 134 (pJP4)" by R. H. Don et al., *J. of Bacteriology*, Vol. 161, No. 1, pp. 85 to 90 (1985), and the Ph.D. thesis of Edward Joseph Perkins, titled, "The Molecular Biology of the Halogenated Aromatic Catabolic Plasmid pJP4," (1987).

The nucleotide sequence of catechol 2, 3-dioxygenase (also known metapyrocatechase) is given by S. Harayama et al., titled, "Evolutionary relationships between catabolic pathways for aromatics: conservation of gene order and nucleotide sequences of catechol oxidation genes of pWWO and NAH7 plasmids, *"Mol. Gen. Genet.* (1987) 210:241–247 and M. Zukowski, "Chromogenic identification of genetic regulatory signals in *Bacillus subtilis* based on expression of a cloned Pseudomonas gene," *Proc. Nat'l Acad. Sci. USA* (1983) 80:1101–1105. This enzyme catalyzes the following reactions:

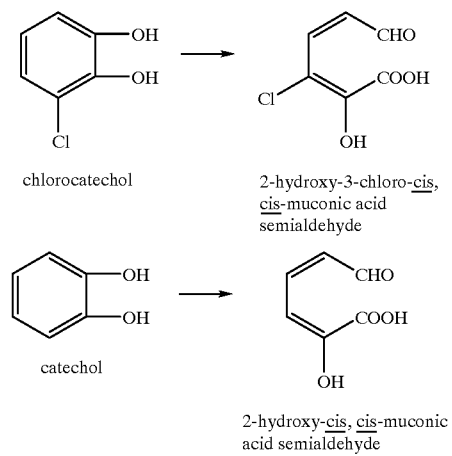

Other ring-cleaving enzymes include pyrocatechase I (catechol 1,2-dioxygenase), which oxidizes catechol to cis, cis-muconic acid and protocatechuate 3,4-dioxygenase (from *Tecoma stans*), which oxidizes protocatechuic acid to 3-carboxy-cis, cis-muconic acid:

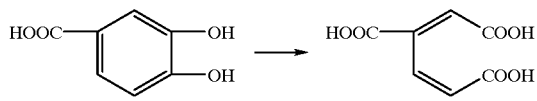

and pyrocatechuic acid to 2-hydroxy-3-carboxy-cis, cis-muconic acid semialdehyde (from *Stizolobium hassjoo*):

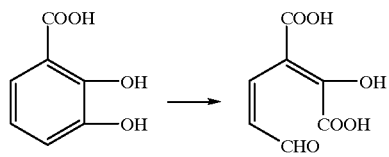

Plants may make resident enzymes that take aromatic compounds to catechols. After the aromatic ring of a catechol has been opened, the products may be harmless or they may be degraded to harmless compounds by other resident plant enzymes. Plants may also polymerize catechols to derivatives of diphenylene dioxide.

Upstream of the ring-opening gene on the plant transformation construct is a eukaryotic promoter that is functional in plants. This is a DNA sequence which acts as a DNA dependent ribonucleic acid (RNA) polymerase binding site and directs and controls the RNA transcription of the ring-opening gene. Eukaryotic promoters are known and are available from those skilled in the art. Eukaryotic promoters can be derived from plants, animals, fungi, certain bacteria or viruses, or they can be wholly synthetic. Examples of promoters that are effective in eukaryotic systems include the CaMV35s promoter from the cauliflower mosiac virus (see U.S. Pat. No. 4,407,956), Nos (nopaline synthase), Mas (mannopine synthase), and Ocs (octopine synthase), found in *Agrobacterium tumefaciens* or *Agrobacterium rhizogenes*, and a promoter derived from the tobacco light-inducible ribulose bisphosphate (RuBP) gene. The CaMV35s promoter is preferred as it is a strong promoter active in most plant tissues. Nucleotide sequences of these promoters are known.

The plant transformation construct also includes a polyadenylic acid addition site which must be downstream of the ring-opening gene. The purpose of the polyadenylic acid addition site is to stabilize the RNA transcript.

OPTIONAL COMPONENTS

The plant transformation construct also preferably contains a selectable marker, which is a gene that expresses an easily detectable trait so that those cells that have been transformed can be readily identified and isolated. A preferred selectable marker is one that confers antibiotic resistance on the cells because transformed cells can then be easily separated from untransformed cells by killing the untransformed cells with the antibiotic. Examples of selectable markers include genes that provide immunity to viruses, mutated aroA gene, which provides glyphosate resistance, gentamicin resistance gene, genes encoding neomycin phosphotransferase II (NPTII), which provides kanamycin or G418 resistance, hygromycin phosphotransferase (HPT), which provides hygromycin resistance, chloramphenicol transacetylase (CAT) which provides chloramphenicol resistance, metallothioneins, which provide resistance to heavy metals, agromycin phosphotransferase, mouse methotrexate-resistant dihydrofolate reductase, phosphinotricine acetyltransferase, nitrilase, and bromoxynil-specific nitrilase.

While a right or left border is not needed if a plant is transformed by a method such as electroporation or microinjection, a right border is needed if transformation is to be accomplished by means of *A. tumefaciens*. The right border should be positioned so that the genes of the construct will be transferred into a plant by virulent Agrobacterium. Generally, this means that the right border is 3' to the ring-opening gene. The right border in the construct is a series of nucleotides which constitutes a recognition site that begins the transfer of the DNA of the construct into the DNA of the plant. The polynucleotide sequences for right borders are known to those skilled in the art and are obtainable therefrom. An example of a right border sequence (one strand of double stranded DNA) is GGCAGGATATATAC-CGTTGTAATTCCGTCCTATATA TGGCAACATTAA, where G is guanine, C is cytosine, A is adenine, and T is thymine. Adjacent sequences necessary for efficient cleavage and transfer should also be included.

If transformation is to be accomplished by means of *A. tumefaciens*, the plant transformation contruct also preferably includes a left border at the left-most position of the construct (i.e., the 3' termination region). The purpose of the left border is to terminate the transfer of DNA from a bacterium containing the construct into the plant cell. All the DNA between the left and right borders (the "T-DNA") is normally inserted into the plant DNA. Left borders are well known in the art and are obtainable from those skilled in the art. An example of suitable left border (single strand sequence) is GGCAGGATATATTCAATTGTAAATC-CGTCCTATATAAGTTAACATTTA.

The plant transformation construct also preferably includes a gene that encodes for a phenol hydroxylase. A phenol hydroxylase is an enzyme that adds a hydroxyl group to a phenol, ortho to the other hydroxyl group, to form a catechol. A phenol hydroxylase is preferably present because the preferred ring-opening gene encodes for an enzyme that can open the aromatic ring of a catechol, and many of the aromatic compounds found in contaminated sites are phenols. Thus, it is useful to include a phenol hydroxylase in the plant transformation construct so that phenols can be converted to catechols which can be degraded by the ring-opening enzyme or which can be further metabolized by enzymes normally present in many plants. Phenol hydroxylases are also known to those skilled in the art and are available therefrom. An example of a phenol hydroxylase is the 2, 4-dichlorophenol hydroxylase from *Alcaligenes eutrophus*. See the Don et al. article and the Perkins thesis, ibid, for an example of a source of the gene encoding this enzyme.

The plant transformation construct also preferably includes a gene that encodes for a cycloisomerase. When the catechol 1,2-dioxygenase opens an aromatic ring, a dicarboxylic acid can be formed. While plants may be able to catabolize the dicarboxylic acid, it is useful to assist in the catabolization by including a gene that encodes for a cycloisomerase. The cycloisomerase forms a lactone from the dicarboxylic acid as illustrated in the following equation.

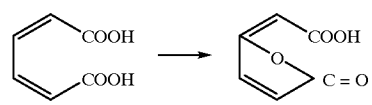

Cycloisomerases are known and are available from those skilled in the art. Examples of suitable cycloisomerases include chloromuconate cycloisomerase, (see Frantz et al., ibid., for nucleotide sequence), clc B gene, and chloromuconate cycloisomerase, tfdD from pJP4. See the Don et al. article and the Perkins thesis, ibid, for an example of a source of a gene encoding this enzyme.

Other genes, which encode improved resistance to pests and pathogens, improved tolerance to weather and poor soil, etc. can also be included in the construct if desired. Thus, the construct has, at a minimum, three components in the order: (eukaryotic promoter)-(ring-opening gene)-(polyadenylic acid addition site). Preferably, the construct has the following components in the order given: (right border)-(polyadenylation site)-(ring-opening gene)-(eukaryotic promoter)-(polyadenylation site)-(selectable marker)-(eukaryotic promoter)-(polyadenylation site)-(phenol hydroxylase-encoding gene)-(eukaryotic promoter)-(left border). Each gene in the construct is preferably provided with its own promoter (upstream) and its own polyadenylic acid addition site (downstream).

The plant transformation construct can be formed by ligation of the genes in the construct to a suitable plant transformation vector according to techniques known to those skilled in the art. Plant cells, which can come from any portion of a plant, including callus or crown gall tumor, as well as plant seeds, propagules, pollen, and plant embryos, can be transformed in various ways using the construct. A feasible method of transforming plants cells is by direct transformation using a tumor inducing (Ti) bacteria. The preferred tumor inducing bacterium is Agrobacterium, although certain other bacteria of the genus Rhizobia, and other bacteria may also be useful. Either *A. tumefaciens* or *A. Rhizogenes* can be used, but *A. tumefaciens* is preferred as it is easier to work with. Agrobacterium can be used to transform virtually all dicotyledonous plants as well as certain monocotyledonous plants. See, for example, U.S. Pat. Nos. 4,658,082; 4,795,855; and 4,459,355, herein incorporated by reference. Once the bacteria containing the vir region have been transformed, the transformation of plant cells is accomplished by using leaf disks as discussed in the accompanying examples.

Transformation of plant cells can also be accomplished by direct injection of the construct DNA into plant cells, such as by microinjection. Other plant transformation techniques may also be suitable, including the use of microprojectiles where a gold or tungsten bullet is coated with the construct and is shot into the plant cells, pollen tube uptake, and electroporation, where plant cell protoplasts are mixed with the construct and transiently subjected to a high electrical potential. Direct DNA uptake using polyethylene glycol, viral infection, liposomes, calcium phosphate, or polycationic substances such as poly-L-ornithine, may also be suitable with protoplasts. For a more detailed description of the transformation of plants, see "Plant Molecular Biology Manual," edited by S. B. Gelvin and R. A. Schilperoort, Cuiver Dordrecht (1988), and the journal *Cell*, vol. 56, Jan. 27, 1989, herein incorporated by reference.

The construct of this invention may be used to transform a variety of eukaryotic plants including gymnosperms and angiosperms. The process works best with angiosperms and members of the dicotyledonous group. Plants that already contain enzymes that degrade aromatics or halogenated aromatics to their respective catechols are also preferred. Examples of suitable plants include poplars, Nicoatiana, black locust, roses, *Tecoma stans*, and *Campsis radicans*. Nicoatiana (tobacco) plants are useful because there is an enormous background of information about them, they grow readily in culture, and they regenerate easily. Poplars are preferred because they grow rapidly (10 to 12 feet a year) on poor soil in a large range of climates, and have extensive root systems that can seek out ground water at depths to about 30 feet. They are dioecious and do not reach sexual maturity until after about 4 to 6 years, so that only females can be planted or the trees can be cut after several years to prevent transgenic pollen from being spread to the environment.

The soil to be treated can be, for example, a landfill, land on which aromatic compounds were spilled, or artificial soil which is wetted with a leachate into which aromatic compounds have been extracted from natural soil. The transformed plant is planted in the soil and is provided with light and any necessary nutrients if not already present. After a period of time which will vary with the effectiveness of the particular transformed plant and its natural and inserted genes, as well as the particular aromatic compounds that are present and their concentration, the aromatic compound concentrations in the soil will fall as they are removed and mineralized by the plant.

The examples which follow further illustrate this invention.

EXAMPLE 1

Growth conditions of bacteria and plasmids. Bacterial strains used in this study are listed in the following table.

| Strains | Plasmid | Marker |
|---|---|---|
| *Escherichia coli* | | |
| HB101 | pSVBRxylE | Carbenicillin |
| MC1000 | pGA642 | Tetracycline |
| " | pGA643 | Tetracycline |
| HB101 | pGWB1 | Carbenicillin |
| " | pEP103 | Carbenicillin |
| *Agrobacterium tumefaciens* | | |
| EHA101 | pEHA101 | Kanamycin |
| GWB100 | pGWB2 | Tetracycline/Kanamycin |
| | pEHA101 | |
| GWB101 | pGWB3 | Tetracycline/Kanamycin |
| | pEAH101 | |
| RPGII | pRPGI | Tetracycline/Kanamycin |
| | pEAH101 | |
| 0CI | p0CI | Tetracycline/Kanamycin |
| | pEAH101 | |

The *E. coli* strains can be obtained from the University of Washington School of Medicine, Seattle, Wash. The *E. coli* pGA642 and pGA643 can be obtained from Dr. Gynheung An at Washington State University, Pullman, Wash. The *A. tumefaciens* strains can be obtained from the University of Washington, School of Medicine, Seattle, Wash. Strain EAH101 is described by Hood et al. (1986) "The Hypervirulence of *Agrobacterium tumefaciens* A281 is Encoded in a Region of pTiBo542 Outside of T-DNA," J. Bact. 168, 1291–1301. *E. coli* strains were maintained on Luria agar plates with the appropriate antibiotics. *Agrobacterium tumefaciens* strains were maintained on AB medium containing antibiotics wherever necessary. Antibiotic concentrations were as follows: For *A. tumefaciens* kanamycin sulfate was used, 50 ug/ml (Sigma Chemical Co., St. Louis, Mo.); carbenicillin, 50 ug/ml (Geopen; Pfizer, New York, N.Y.); and tetracycline hydrochloride, 25 ug/ml (Sigma). For *E. coli* tetracycline hydrochloride, 25 ug/ml and carbenicillin, 50 ug/ml was used.

Preparation of DNA from *E. coli* and *A. tumefaciens*. Plasmid DNA of *A. tumefaciens* and *E. coli* was isolated by the alkaline lysis method of Birnboim and Doly modified by resuspending the pellet in 0.8M NaCl after phenol extraction and ethanol precipitation. To precipitate the plasmid DNA, polyethylene glycol (M.W. 6000, Sigma) from a 13% (w/v) stock solution was added to give a final concentration of 6.5% (w/v). The precipitated plasmid DNA was collected by centrifugation and the pellet was washed twice with 70% (v/v) ethanol and dried by evaporation under vacuum. The resulting DNA pellet was resuspended in 10 mM trihydroxyaminomethane hydrochloric (TRIS·HCl) acid, pH 7.8 buffer containing 1 mM ethylenediamine tetraacetic acid (EDTA).

Agarose gel electrophoresis. Restriction endonucleases and DNA modifying enzymes were purchased from Bethesda Research Laboratories, Inc. (Gaithersburg, Md.), New England BioLabs, Inc. (Beverly, Mass.) and International Biotechnologies, Inc. (New Haven, Conn.) and were used as recommended by the suppliers. Agarose gel electrophoresis was performed as described by Maniatis et al., "Molecular Cloning: a Laboratory Manual."

Construction of Agrobacterium Strains Used to Transform Plant Tissues. A gene encoding the chlorocatechol 1,2-dioxygenase (Cl,2-0), clcA from *Pseudomonas putida* plasmid pAC27 (Frantz et al. PNAS 1987), was obtained from A. Chakrabarty, University of Illinois, Chicago, Ill. The nucleotide sequence of the pAC27 gene is given in two articles: (1) D. Ghosal and You, "Nucleotide Homology and Organization of Chlorocatechol Oxidation Genes of Plasmids, pJP4 and pAC27," *Mol. Gen. Genet.* 211: 113–120(1988) and (2) B. Frantz et al., "Organization and Nucleotide Sequence Determination of a Gene Cluster Involved In 3-Chlorocatechol Degradation," *Proc. Natl. Acad. Sci. U.S.A.* 84(13) 4460-4(1987). It was cloned as a 1.3 kilobase pair EcoR1-HindIII restriction fragment from the plasmid pDC100 (obtained from A. Chakrabarty) into the polylinker site of pBluescript (a cloning vector from Stratagene, Inc., La Jolla, Calif.). Ligations to join DNA fragments were performed as described in Maniatis et al., Molecular Cloning, Cold Spring Harbor, 1982. Transformation of ligated plasmid into bacteria was accomplished as described by Hanahan, J. Mol. Biol. 166:557–580. This resulted in ClaI-HindIII restriction endonuclease sites bracketing the Cl,2-0 gene. The Cl,2-0 gene was then inserted in a similar manner into pGA642 and pGA643 to produce plasmids pRPGII and pOC1. The plant transformation vectors pGA642 and pGA643 contain an antibiotic resistance gene expressed in plants, neomycin phosphotransferase, the nopaline synthase promoter (pGA642) or the Cauliflower mosaic virus 35s promoter (pGA643), a multiple cloning site for insertion of desired genes, and a polyadenylation site—all of which are situated between right and left T-DNA border sequences derived from the *A. tumefaciens* pTiA6 plasmid. These plasmids were transformed into the *A. tumefaciens* strain EHA101 by the freeze thaw method. Holsters M., de Waele D., Depicker A., Messens E., VanMontagu M., Schell J. 1978, "Transfection and Transformation of *A. Tumefaciens*," Mol. Gen. Genet.-163:181–187.

A structural gene, xylE, encoding catechol 2,3-dioxygenase (C2,3-0) contained in the plasmid pSVBRxylE, a gift from Tom Hollen, Dept. Biochemistry, Univ. of Washington, was cloned as a 1.25 kilobase pair (kbp) PstI-HindIII fragment from plasmid pSVBRxylE into the polylinker site of plasmid pUC19 (available from New England Biolabs) giving rise to plasmid pGWB1. Plasmid pSVBRxylE was prepared from the plasmid pWWO, which contains the xylE gene. The plasmid pWWO is described in an article by S. Harayama et al., titled, "Evolutionary Relationships Between Catabolic Pathways for Aromatics: Conservation of Gene Order and Nucleolide Sequences of Catechol Oxidation Genes of pWWO and NAH7 Plasmids," *Mol. Gen. Genet* (1987) 210:241 to 247. The nucleotide sequence of the xylE gene is given in two articles: (1) Harayama et al., id., and (2) an article by Mark M. Zukowski, "Chromogenic Identification of Genetic Regulatory Signals in *Bacillus Subtilis* Based on Expression of a Cloned Pseudomonas Gene," *Proc. Nat'l Acad. Sci. USA*, Vol. 80, pp 1101–1105, Feb. 1983. To proliferate this plasmid and obtain sufficient amounts of C2,3-0 DNA for subsequent constructions, the plasmid was transferred into *E. coli* strain HB101 by the procedure of Hanahan, *J. Mol. Biol.* 166:557–580. The C2,3-0 gene was removed from the plasmid pGWB1 by digestion with restriction endonucleases KpnI and HindIII. This approximately 1.25 kbp fragment of C2,3-0 DNA was inserted into the corresponding restriction sites of plasmids pGA642 and pGA643 to produce plasmids pGWB2 and pGWB3, respectively. The plant transformation construct pGWB2 includes an antibiotic resistance gene, neomycin phosphotransferase that is expressed in plants, the nopaline synthase (nos) gene promoter, the C2,3-0 gene, and polyadenylic acid addition sequence, all of which are situated between the right and left border sequences of the T-DNA derived from the *A. tumefaciens* pTiA6 plasmid. The construct pGWB3 is the vector pGA643 where the nos gene promoter has been replaced by the 35S cauliflower mosaic virus promoter. These plasmids were transformed into *Agrobacterium tumefaciens* strain EHA101 by the freeze-thaw method resulting in *A. tumefaciens* strains GB100 (EAH101/pGWB2) and GB101 (EHA101/pGWB3). Identification of the bacterial strains pGB100 and GB101 expressing the C2,3-0 gene was achieved by spraying the bacterial colonies with 0.5M solution of catechol and picking those colonies that turned yellow in response to the application of catechol. The presence of plasmids pGWB2 and pGWB3 in these strains was further confirmed by isolation and restriction endonuclease analysis of the plasmid DNA.

Construction of pRPGII and pOC1

The gene encoding the Cl,2-0 enzyme was cloned into plant gene expression vectors for transfer into plants. This was accomplished by ligating a 1.3 Kb EcoRI-HindIII fragment from plasmid pDC100, which contains the Cl,2-0 gene (clcA), into the EcoRI-HindII sites of the cloning vector pBluescript. This resulted in a ClaI site before clcA and an XbaI site following clcA. The 1.3 Kb ClaI-XbaI fragment from this construct was then ligated into the plant gene expression vectors pGA642 and pGA643. Two clones were created. One, pRPGII, carried clcA cloned behind the nos promoter and a second, pOC1, carrying the clcA driven by the CaMV 35s promoter. The plasmids were subsequently transferred into *A. tumefaciens* EHA101 creating strains RPGII and OC1, respectively. These Agrobacterium strains were used for transfer of the Cl,2-0 into plants.

Plant growth conditions and transformation by Agrobacterium.

Tobacco, *Nicotiana glauca* and *N. tobbacum* var. xanthi, n.c., plants were grown from seeds in a controlled environment growth room for 3 to 4 weeks. Fully expanded leaves were taken from the plants, sterilized using a solution of 1.5% (v/v) sodium hypochlorite, and then rinsed in sterile distilled water. Disks, 4 mm, were cut from the tissue using a paper punch. The leaf disks were transformed by *Agrobacterium tumefaciens* strains GB100 and GB101 employing the procedure of Horsch et al., *Science* 227:1229–1231. Transformed leaf disks were cultured on agar plates with MS medium for 2 to 3 days and then on similar medium containing 250 ug/ml kanamycin sulfate to select for transformed tissues containing the gene encoding neomycin phosphotransferase; 200 ug/ml cefotaxime (Claforan; Hoechst-Roussel Pharmaceuticals, Inc., Somerville, N.J.) was used to kill residual bacteria. Shoots from the leaf dishes were distinguished and selected by the activity of the incorporated neomycin phosphotransferase gene. Only transgenic tissue can grow in the presence of 250 $\mu$g/ml of kanamycin sulfate. Transformation and regeneration of a transgenic tobacco plant is simply achieved through routine laboratory methods as outlined in Horsch et al., 1985. [Horsch, R. D., Fry, T. E., Hoffman, N. L., Eichholtz, D., Rogers, S. G., and Fraley, R. T. (1985), "A Simple and General Method for Transferring Genes into Plants," *Science*, 227, 1229–1231.]

EXAMPLE 2

Experiments were performed to determine if the catechol dioxygenase enzyme is expressed and active in the transgenic plants described in Example 1. Leaf disks from the following plants were prepared and grown on solid callus medium in the presence of various concentrations of catechol.

| Control | Untransformed Xanthi |
|---|---|
| GB101 #55 | CaMV promoter, catechol 2,3-dioxygenase |
| RPGII #27 | nos promoter, chlorocatechol 1,2-dioxygenase |
| OCI #15 | CaMV promoter, chlorocatechol 1,2-dioxygenase |

Leaf disks from plants carrying a dioxygenase gene were more sensitive to high concentrations of catechol (greater than 50 ug/ml) than disks from control plants.

Leaf disk from wild-type tobacco have a high tolerance for catechol. Since the presence of a dioxygenase gene in the plant genome confers sensitivity (i.e., a slight yellowing—the tissue did not die) to high levels of catechol, it is reasonable to conclude that the plants are more sensitive to the 2-hydroxy-cis, cis-muconic semialdehyde or to cis, cis-muconic acid products resulting from the dioxygenase activity. It is important to point out that there appears to be no effect on growth at lower levels of catechol, so it may be that only high levels of the products are toxic to isolated leaf tissues. At higher levels of catechol the inclusion of a gene that encodes for a cycloisomerase may alleviate or eliminate this problem. Intact normal or transgenic tobacco plants containing catechol 1,2-dioxygenase or catechol 2,3-dioxygenase encoding genes showed no significant differences in sensitivity towards catechol and showed no visible damage at concentrations of up to 0.5 millimolar.

Both control and transgenic tobacco plants containing the catechol 2,3-dioxygenase gene were grown in vitro on M$^-$ medium. After 2–3 days for adjustment to liquid medium, the old medium was replaced with 25 ml. of fresh medium with the addition of the radioactive $^{14}C$ catechol (Sigma Chemical Co.) to see if the transgenic plants were able to catabolize it. The plant chambers were kept in darkness by wrapping the containers with aluminum foil to avoid reutilization of $CO_2$ evolved during respiration by the plant. The $CO_2$ was collected in barium hydroxide as barium carbonate. The incubation of both the control plants and the transgenic plants was carried out for 48 hours. After the completion of the experiments, the precipitates of barium carbonate were analyzed for radioactivity by liquid scintillation. The total radioactivity (counts) added was $1.11 \times 10^7$ counts/min.

| | Counts observed after 48 hours | |
|---|---|---|
| | $CO_2$ Evolved (counts/min/mg of $BaCO_3$) | Medium (counts/25 ml) |
| Control | 17.9 | 450,000 |
| Transgenic | 47.6 | 385,000 |

These results indicate that the transgenic plants of this invention have an enhanced ability to convert catechol into $CO_2$. It is important to note that the experiments were conducted axenically so that the evolution of $CO_2$ was due only to the metabolic activity of the plants. The above table shows that the transgenic plants were more than 2.6 times as effective as the untransformed plants in converting catechol into $CO_2$.

The experiments were repeated three times. The radioactivity level of the precipitated $BaCO_3$ was counted and the radioactivity count was certain to ±10%. The statistical treatment of Loevinger and Berman [Loevinger, R., and Berman, M. (1951), Nucleomics 9, 26] was used to correct for background and to insure a low standard error. The differences in specific activities of the precipitated BaCO3 were examined by the Student T test and are significant at greater than 99%, i.e., the probability is less than one in a hundred that the difference between 17.9±2 and 47.6±5 is due to chance.

EXAMPLE 3

It is shown that the plant transformation construct containing the ring-opening gene is heritable and is expressed in progeny of the transformed plants. In these experiments the kanamycin resistance of the progeny from selfed plants was determined as a simple means to follow the transmission of the incorporated genes. Two plants each gave rise to progeny three quarters of which were resistant and one quarter sensitive to kanamycin. The seeds were surface sterilized with bleach, 5% sodium hypochlorite for 5 minutes, followed by 70% ethanol for 1 minute. The seeds were germinated on M$^-$ medium containing 100 mg/ml of kanamycin.

EXAMPLE 4

Following the procedures described in the preceding Examples, *Nicotiana tabacum* var. Xanthi transformed with both the tfdB gene, which encodes 2,4-dichlorophenol hydroxylase, and the tfdC gene, which encodes chlorocatechol 1,2-dioxygenase, were prepared. These genes were obtained from plasmid pJP4 from *Alcaligenes eutrophus*. Two independently generated plants transformed with these genes were exposed to $^{14}C$-2,4-dichlorophenol (2,4DCP) in hydroponics for 24 hours. After exposure, plants were frozen at −70° C. Root, stem, and leaf tissues of one plant

We claim:

1. A plant transformation construct comprising the following DNA elements operably joined in a 5' to 3' direction:

(a) a transcriptional initiation regulatory element functional in plants;

(b) a structural gene encoding a catechol dioxygenase; and (c) a transcriptional termination regulatory element functional in plants.

2. A plant transformation construct according to claim 1 having a T-DNA right border sequence in an orientation such that the construct will be transferred into a plant by virulent Agrobacterium.

3. A plant transformation construct according to claim 2 having a T-DNA left border sequence in an orientation so as to terminate transfer of the construct into a plant by virulent Agrobacterium.

4. A plant transformation construct according to claim 1 wherein said structural gene encoding a catechol dioxygenase gene is obtained from bacteria of the genus Pseudomonas.

5. A plant transformation construct according to claim 1 wherein said DNA is double stranded.

6. A plant transformation construct according to claim 1 wherein said catechol dioxygenase is catechol 2,3-dioxygenase.

7. A plasmid useful for transforming plant cells having a plant transformation construct according to claim 1 as part of its transferred DNA.

8. A bacterial species that contains a plasmid according to claim 7.

9. A bacterial species according to claim 8 where said species is *Agrobacterium tumefaciens*.

10. A transgenic plant cell containing, as part of its genome, a plant transformation construct according to claim 1.

11. A transgenic plant whose progenitor is a transgenic plant cell according to claim 10.

12. A transgenic plant according to claim 11 of the genus Nicotiana.

13. A transgenic plant according to claim 11 of the genus Populus.

14. A method of degrading aromatic compounds in soil comprising planting in said soil a transgenic plant according to claim 11.

15. A plant transformation construct according to claim 1 wherein said catechol dioxygenase is chlorocatechol 1,2-dioxygenase.

16. A plant transformation construct according to claim 1, which includes a marker for selection of plant transformation events, said marker comprising the following DNA elements operably joined in a 5' to 3' direction:

(a) a transcriptional initiation regulatory element functional in plants;

(b) a structural gene encoding an enzyme conferring plant resistance to a selective agent; and (c) a transcriptional termination regulatory element functional in plants.

17. A plant transformation construct according to claim 1 which includes DNA comprising the following elements operably joined in a 5' to 3' direction:

(a) a transcriptional initiation regulatory element functional in plants;

(b) a structural gene encoding an enzyme capable of hydroxylating phenols; and (c) a transcriptional termination regulatory element functional in plants.

18. A plant transformation construct according to claim 1 which includes DNA comprising the following elements operably joined in a 5' to 3' direction:

(a) a transcriptional initiation regulatory element functional in plants;

(b) a structural gene encoding a chloromuconate cycloisomerase enzyme; and (c) a transcriptional termination regulatory element functional in plants.

19. A plant transformation construct comprising the following structural genes, operably joined in a 5' to 3' direction:

(a) a left T-DNA border sequence;

(b) a transcriptional initiation regulatory element functional in plants;

(c) a structural gene encoding an enzyme capable of hydroxylating phenols;

(d) a transcriptional termination regulatory element functional in plants;

(e) a transcriptional initiation regulatory element functional in plants;

(f) a structural gene encoding an enzyme capable of conferring resistance to a selective agent;

(g) a transcriptional termination regulatory element functional in plants;

(h) a transcriptional initiation regulatory element functional in plants;

(i) a structural gene encoding a catechol dioxygenase enzyme;

(j) a transcriptional termination regulatory element functional in plants; and (k) a right T-DNA border sequence.

20. A plant transformation construct according to claim 1 wherein said structural gene encoding a catechol dioxygenase is xylE.

21. A plant, transformation construct according to claim 1 wherein said structural gene encoding a catechol dioxygenase is clcA.

22. A plant transformation construct according to claim 1 wherein said structural gene encoding a catechol dioxygenase is tfdC.

23. A plant transformation construct according to claim 17 wherein said structural gene encoding an enzyme capable of hydroxylating phenols is tfdB.

* * * * *